US011123017B2

United States Patent
Kuruganti et al.

(10) Patent No.: US 11,123,017 B2
(45) Date of Patent: Sep. 21, 2021

(54) ADAPTERS FOR USE WITH DYNAMOMETER FOR SUBJECTS HAVING LIMB IMPAIRMENT

(71) Applicant: UNIVERSITY OF NEW BRUNSWICK, Fredericton (CA)

(72) Inventors: Usha Kuruganti, Fredericton (CA); Victoria Chester, Keswick (CA)

(73) Assignee: UNIVERSITY OF NEW BRUNSWICK, Fredericton (CA)

( * ) Notice: Subject to any disclaimer, the term of this patent is extended or adjusted under 35 U.S.C. 154(b) by 500 days.

(21) Appl. No.: 15/946,295

(22) Filed: Apr. 5, 2018

(65) Prior Publication Data
US 2018/0289331 A1 Oct. 11, 2018

Related U.S. Application Data

(60) Provisional application No. 62/481,988, filed on Apr. 5, 2017.

(51) Int. Cl.
*A61B 5/00* (2006.01)
*A63B 21/002* (2006.01)
(Continued)

(52) U.S. Cl.
CPC ............ *A61B 5/702* (2013.01); *A61B 5/1121* (2013.01); *A61B 5/458* (2013.01); *A61B 5/4585* (2013.01);
(Continued)

(58) Field of Classification Search
CPC ......... A61B 7/02; A61B 5/458; A61B 5/4585; A61B 5/1121; A61B 2505/09; A63B 1/00;
(Continued)

(56) References Cited

U.S. PATENT DOCUMENTS 5,196,956 A 3/1993 Sugiura
5,277,684 A 1/1994 Harris
(Continued)

OTHER PUBLICATIONS

Judith Davidson, A comparison or upper limb amputees and patients with upper limb injuries using the disability of the arm, shoulder and hand (DASH), From "MEC '05 Intergrating Prosthetics and Medicine", Proceedings of the 2005 MyoElectric Controls/Powered Prosthetics Symposium, held in Fredericton, New Brunswick, Canada, Aug. 17-19, 2005, 9 pages.

(Continued)

*Primary Examiner* — Devin B Henson
*Assistant Examiner* — Joseph A Tombers
(74) *Attorney, Agent, or Firm* — Hill & Schumacher

(57) ABSTRACT

Attachments for isokinetic dynamometers and methods of use thereof are provided for use with subjects having limb impairments. An example dynamometer attachment for use with a subject having an impaired limb includes a frame that has fixed thereto a padded limb support, where the padded limb support is configured to secure an impaired limb of the subject. The padded limb support includes a securing mechanism for securing the impaired limb relative to the frame, and the frame is connected to the dynamometer lever arm via an intermediate connector assembly. The connector assembly permits translation of the padded limb support in at least two dimensions relative to the lever arm prior to securing the frame fixedly in place. The translation adjustability of the attachment facilitates the alignment of the dynamometer attachment to the limb or partial limb of the subject without requiring movement of the subject.

20 Claims, 9 Drawing Sheets

(51) Int. Cl.
*A61B 5/11* (2006.01)
*A63B 1/00* (2006.01)

(52) U.S. Cl.
CPC .............. *A63B 1/00* (2013.01); *A63B 21/002* (2013.01); *A61B 2505/09* (2013.01)

(58) Field of Classification Search
CPC ............ A63B 21/002; A63B 23/03508; A63B 2208/0252; A63B 71/0009; A63B 21/4039; A63B 2213/004; A63B 21/4017; A63B 21/4033; A63B 23/1281; A63B 2209/00; A63B 2220/833; A63B 2220/51; A63B 2209/14; A63B 2209/10; A63B 2220/803; A63B 2225/09; A63B 24/0087
See application file for complete search history.

(56) References Cited

U.S. PATENT DOCUMENTS

| | | | |
|---|---|---|---|
| 6,342,033 | B1 | 1/2002 | Walker |
| 2008/0216570 | A1* | 9/2008 | Andres .................. A61B 5/224 73/379.01 |
| 2015/0360069 | A1* | 12/2015 | Marti ............... A63B 23/03508 482/6 |
| 2016/0107021 | A1 | 4/2016 | Bakrac et al. |

OTHER PUBLICATIONS

Judith Davidson, A comparison or upper limb amputees and patients with upper limb injuries using the disability of the arm, shoulder and hand (DASH), Disability and Rehabilitation, 2004, 917-923, 26.

Liselotte M. Hermansson et al., Assessment of capability for myoelectric control: a new rasch-built measure of prosthetic hand control, Journal of Rehabilitation Medicine, 2005, 166-171, 37.

Virginia Wright, Prosthetic outcome measures for use with upper limb amputees: a systematic review of the peer-reviewed literature, 1970-2009, American Academy of Orthotists & Prosthetists, 2009, 3-63, 21(4S).

Helen Y.N. Lindner et al., Assessment of capacity for myoelectric control: evaluation of construct and rating scale, Journal of Rehabilitation Medicine, 2009, 467-474, 41.

Biodex Operation Manual, System 3 and 4 Upper Extremity Hemiparetic Attachment Set, Printed Sep. 25, 2016, Shirley, New York, 1-24.

Biodex Brochure, New Hemiparetic Attachments, Expand the use of your Dynamometer, New specialized hemiparetic upper extremity attachments promote neuro recovery and improve strength, Shirley, New York, Printed Sep. 25, 2014, 1-4.

Carolynn Patten et al., Concurrent neuromechanical and functional gains following upper-extremity power raining post-stroke, Journal of Neuroengineering and rehabilitation, 2013, 1-19, 10(1).

Carolynn Patten et al., Reliability and responsiveness of elbow trajectory tracking in chronic poststroke hemiparesis, Journal of Rehabilitation Research & Development, 2003, 487-500, 40(6).

Usha Kuruganti et al., The development of an isokinetic adapter for prosthesis users, New Brunswick Health Research Foundation Research Day (Poster), Nov. 13-14, 2014.

Usha Kuruganti et al., The development of an isokinetic adapter for prosthetis users, New Brunswick Health Research Foundation Research Day (Abstract), Nov. 13-14, 2014.

CSMI Medical Solutions Manual, Humac Norm, Testing & Rehabilitation System, Measure & Improve Performance Manual, undated.

J. Raad, Rehab Measures—Hand Held Myometry/Dynamometry. The Rehabilitation Measures Database. Retrieved May 27, 2014.

J. Raad, Rehab Measures—Hand Held Myometry/Dynamometry. The Rehabilitation Measures Database. Retrieved Oct. 6, 2016.

* cited by examiner

SIDE VIEW

SECTION A-A

TOP VIEW

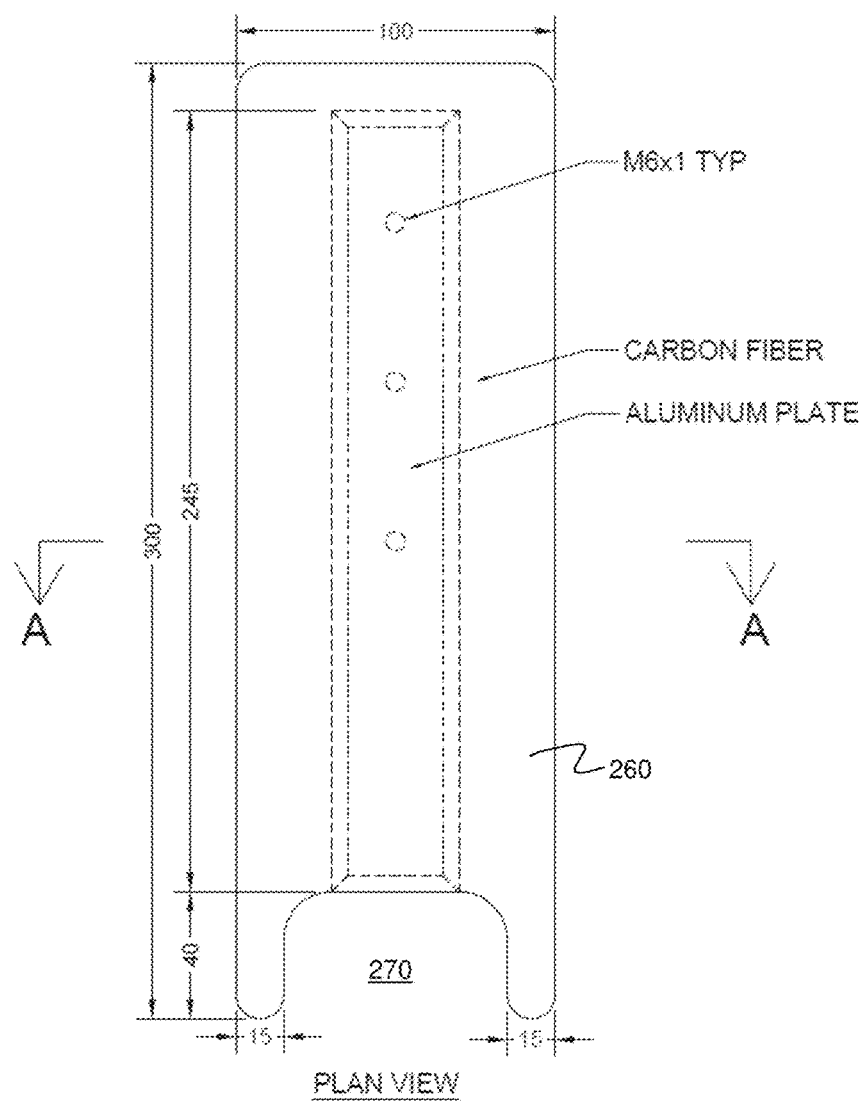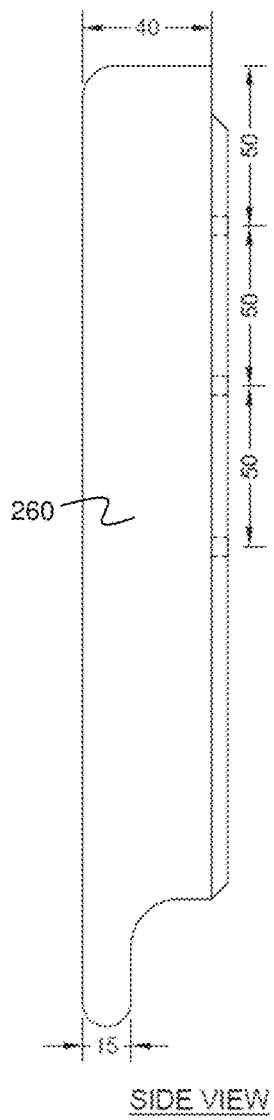
FIG. 7A
FIG. 7B
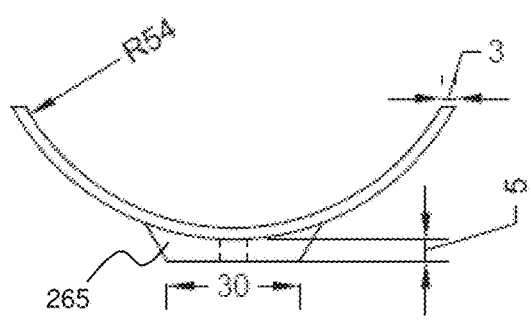
FIG. 7C
SECTION A-A

ADAPTERS FOR USE WITH DYNAMOMETER FOR SUBJECTS HAVING LIMB IMPAIRMENT

CROSS-REFERENCE TO RELATED APPLICATION

This application claims priority to U.S. Provisional Application No. 62/481,988, titled "ADAPTERS FOR USE WITH DYNAMOMETER FOR SUBJECTS HAVING LIMB IMPAIRMENT" and filed on Apr. 5, 2017, the entire contents of which is incorporated herein by reference.

BACKGROUND

The present disclosure relates to equipment for exercise, physiological assessment and rehabilitation. More particularly, the present disclosure relates to isokinetic dynamometers and dynamometer attachments.

Isokinetic dynamometers are used to measure strength during isokinetic contractions, which are movements in which the angular velocity of a displaced body segment is kept constant. Isokinetic dynamometers are exercise machines in which the load is controlled by gears or friction systems, and such devices are used extensively with healthy and rehabilitation populations to study strength. Isokinetic dynamometers can be used to perform both shortening and lengthening contractions and are used to quantify the torque, work and power output of muscle. One example of a commercially available isokinetic dynamometer is the Cybex Humac Norm (CSMI) system.

One advantage of using an isokinetic dynamometer for rehabilitation monitoring is that the subject can simply stop in the middle of an exercise without having to worry about controlling the load (therefore when there is no stress on the load, the dynamometer stops). In addition, because these systems are accommodating, the resistance provided by the device varies in proportion to the capabilities of the user over the range of motion.

SUMMARY

Attachments for isokinetic dynamometers and methods of use thereof are provided for use with subjects having limb impairments. An example dynamometer attachment for use with a subject having an impaired limb includes a frame that has fixed thereto a padded limb support, where the padded limb support is configured to secure an impaired limb of the subject. The padded limb support includes a securing mechanism for securing the impaired limb relative to the frame, and the frame is connected to the dynamometer lever arm via an intermediate connector assembly. The connector assembly permits translation of the padded limb support in at least two dimensions relative to the lever arm prior to securing the frame fixedly in place. The translation adjustability of the attachment facilitates the alignment of the dynamometer attachment to the limb or partial limb of the subject without requiring movement of the subject.

Accordingly, in a first aspect, there is provided a dynamometer attachment for use with a subject having a limb impairment, the dynamometer attachment comprising:
 a frame;
 a padded limb support fixed to said frame, wherein said padded limb support is configured to receive and removably secure an impaired limb of the subject; and
 a connector assembly for connecting said frame to a lever arm of a dynamometer, wherein the connector assembly is configured to permit translation of said frame in two dimensions relative to the lever arm, thereby facilitating alignment of said padded limb support with the impaired limb while aligning a joint of the subject with a rotational axis of the dynamometer.

In another aspect, there is provided a dynamometer system for use with a subject having a limb impairment, the dynamometer system comprising:
 a dynamometer;
 a lever arm connected to said dynamometer, said lever arm comprising at least a proximal lever arm portion extending along a lever axis perpendicular to a rotation axis of said dynamometer;
 a frame;
 a padded limb support fixed to said frame, wherein said padded limb support is configured to receive and removably secure an impaired limb of the subject; and
 a connector assembly for connecting said frame to a distal portion of said lever arm, wherein the connector assembly is configured to permit translation of said frame in a first direction parallel to the rotation axis and a second direction perpendicular to the lever axis and perpendicular to the rotation axis, thereby facilitating alignment of said padded limb support with the impaired limb while aligning a joint of the subject with a rotational axis of said dynamometer.

In another aspect, there is provided a method of aligning a subject with a dynamometer prior to performing a movement involving a joint associated with an impaired limb of the subject, the method comprising:
 providing a dynamometer system as described above;
 positioning the subject such that the joint is aligned with the rotation axis of the dynamometer;
 translating the connector assembly relative to the lever arm in the first direction to align the padded limb support with the impaired limb;
 translating the frame relative to the connector assembly in the second direction to further align the padded limb support with the impaired limb;
 employing the connector assembly to lock the position of the connector assembly relative to the lever arm in the first direction;
 employing the connector assembly to lock to position of the frame relative to the connector assembly in the second direction; and
 securing the impaired limb to the padded limb support.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 7A-C show different views of a limb support that forms a component of an example dynamometer attachment, where the dynamometer attachment is configured for use with a subject having an impaired limb, and where the limb support is configured to be secured to the frame shown in FIGS. 5A-C, and to include a padding and restraining mechanism (not shown).

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1A:
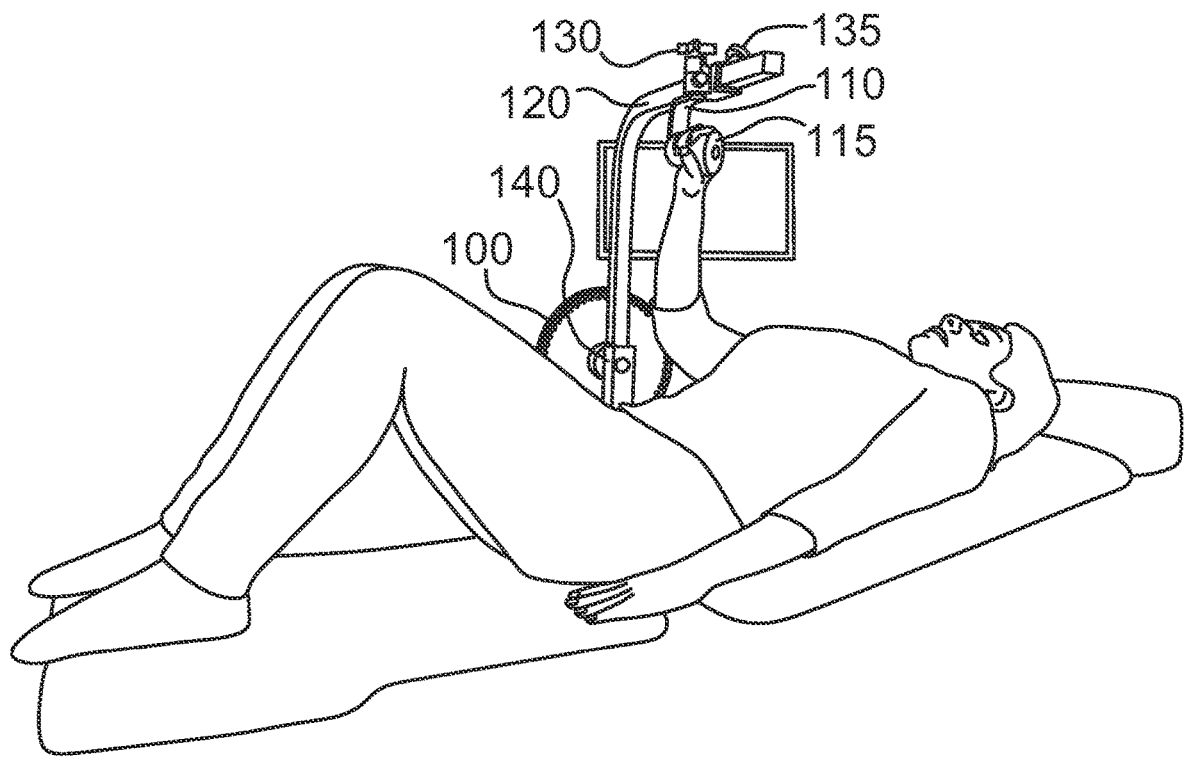
FIG. 1A shows a subject performing a movement with a dynamometer using a conventional elbow flexion/extension attachment.
Figure 1B:
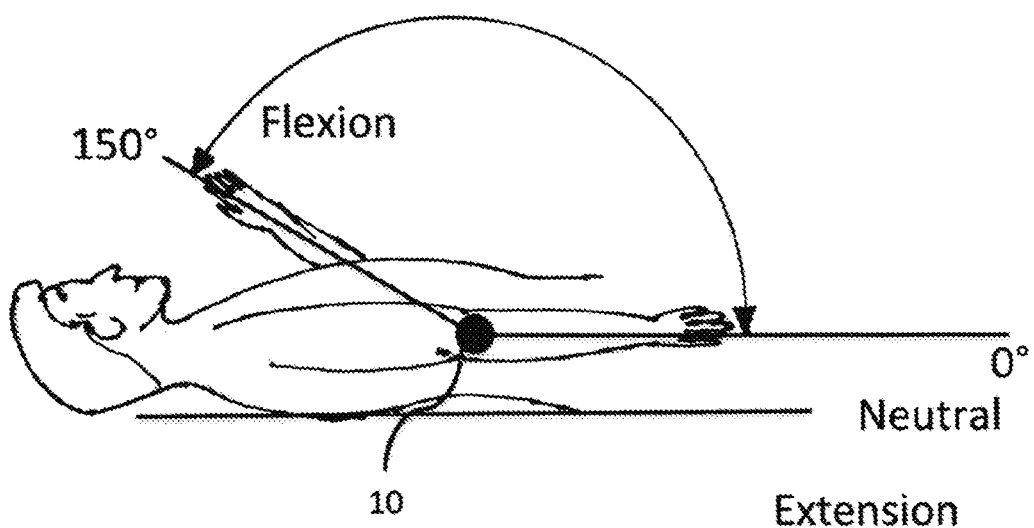
FIG. 1B illustrates an elbow flexion/extension movement performed using an isokinetic dynamometer.

Referring now to FIG. 1A, an example isokinetic dynamometer is shown being used by a subject to perform an isokinetic elbow flexion/extension movement. The movement is illustrated in FIG. 1B, showing the motion of the arm relative to the elbow joint 10. As explained above, the dynamometer maintains a constant velocity during performance of the movement by applying a suitable restoring force, while measuring the applied force.

The dynamometer 100 shown in FIG. 1A includes a conventional elbow flexion/extension attachment 110. The subject 20 grips a handle of the attachment 110, which allows the subject to apply a force to the dynamometer during the flexion/extension movement. The attachment 110 is secured to the lever arm 120 of the dynamometer 100 by a connector 130, enabling the attachment 110 to be positioned relative to the rotational axis of the dynamometer 100. A second connector 135 permits rotational positioning of the handle 115 of the attachment 110 relative to the lever arm 120. The lever arm 120 is connected to the dynamometer 100 by another connector 140, which allows the lever arm to be varied in length relative to the rotation axis.

While the attachment 110 is well adapted for subjects having full control and mobility of their upper limbs, it is unfortunately ill adapted for individuals who have a limb impairment, such as, but not limited to, an amputation, hemiparesis, congenital limb deformity, limb injury, compromised limb function, or other limb pathology. For example, the attachment 110 shown in FIG. 1A is only suitable for subjects having an intact and functioning limb, as the device requires gripping of the handle during the movement in order to apply the necessary force (torque) to the lever arm.

There is currently a lack of availability of dynamometer attachments for subjects with limb impairments. Furthermore, quantitative clinical assessment of such subjects has been challenging due to the complexity of the muscle physiology of those with amputations and other impairments. In addition, most clinical research has focused on studying isometric (stationary) limb movements. In order to develop more robust systems, attachments suitable for impaired limbs are needed to study muscle mechanics of those with amputations and other limb impairments under dynamic (moving) movements.

Various example embodiments of the present disclosure provide attachments for isokinetic dynamometers, isokinetic dynamometer systems, and methods of use thereof that are adapted for subjects with limb impairments. The example adapters described herein, and variations and adaptations thereof, may be beneficial in enabling the use of isokinetic dynamometers (e.g. commercial dynamometers and dynamometers satisfying industry standards) by subjects having limb impairments, where the attachments facilitate the application of force by the subject during isokinetic elbow flexion and extension (e.g. during isokinetic strength measures or exercises).

In some embodiments, the example attachments described herein may thus be employed by subjects with limb amputations (with or without their prosthesis) in order to produce reliable strength measures with a dynamometer. In other example embodiments, the various example embodiments described herein may additionally or alternatively be employed by subjects with other types of impairments, such as hemiparesis, congenital limb deformities, limb injuries, compromised limb function, or other limb pathologies.

The ability to adapt a dynamometer attachment for use with subjects having upper limb impairments opens new diagnostic and therapeutic strength testing modalities for this population. Moreover, the ability to obtain accurate strength measures in a safe and accurate manner may be beneficial in developing targeted strength training protocols for these individuals that will help with their long-term health. Limb amputations can have a significant impact on daily functions and affect the quality of life of an individual. Understanding the strength limitations of both intact and amputated limbs can help to develop more robust rehabilitation protocols.

The various example embodiments described herein may also be employed by able-bodied subjects, as an alternative to use of conventional dynamometer attachments. For example, dynamic force measures obtained using the attachments described herein by able-bodied subjects (or variations thereof) may be employed as reference data for comparison with dynamic force measures obtained by subjects having limb impairments.

Figure 2:
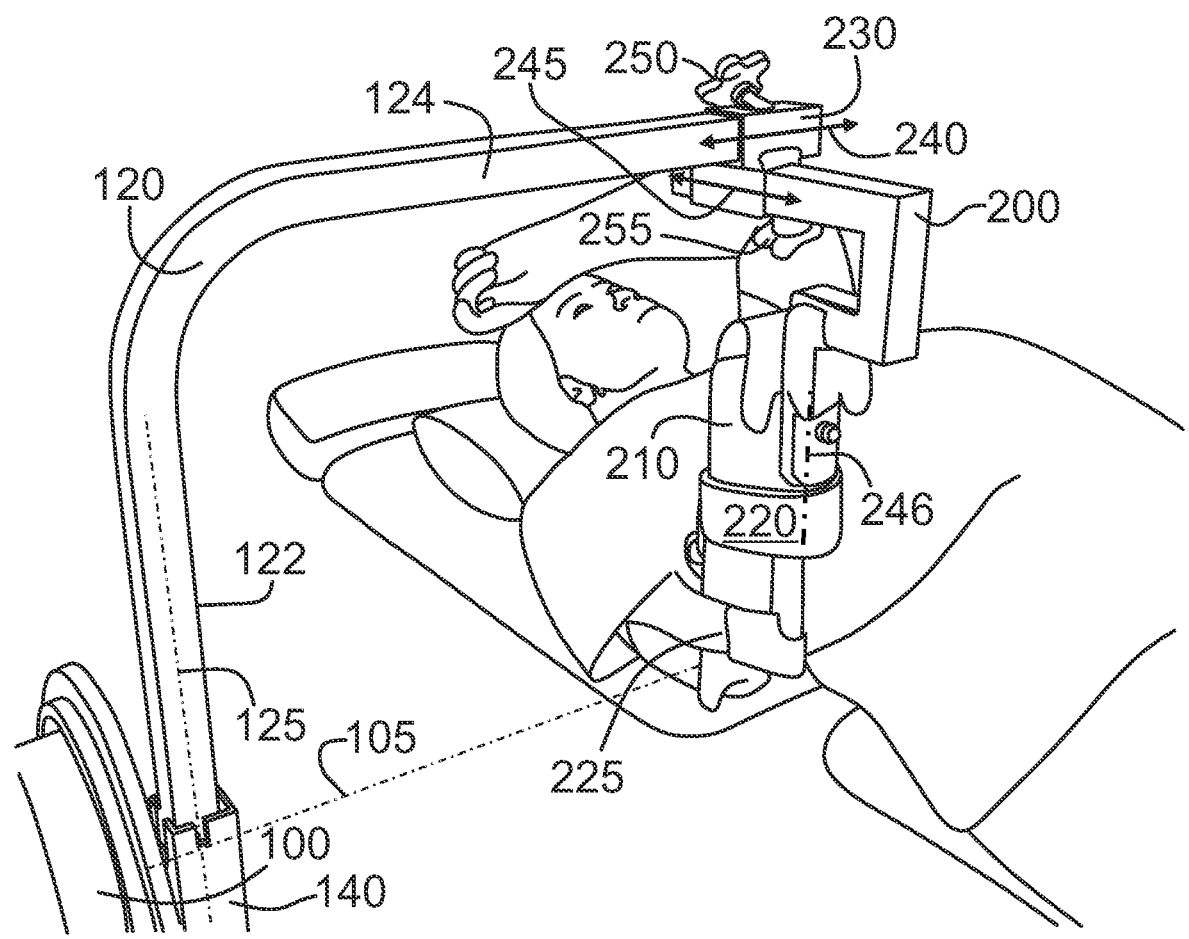
FIG. 2 is a photograph of a subject with an amputation below the elbow performing an elbow flexion/extension movement using an attachment configured to support an impaired limb, showing the connection of the attachment to the lever arm of the dynamometer.
Figure 3:
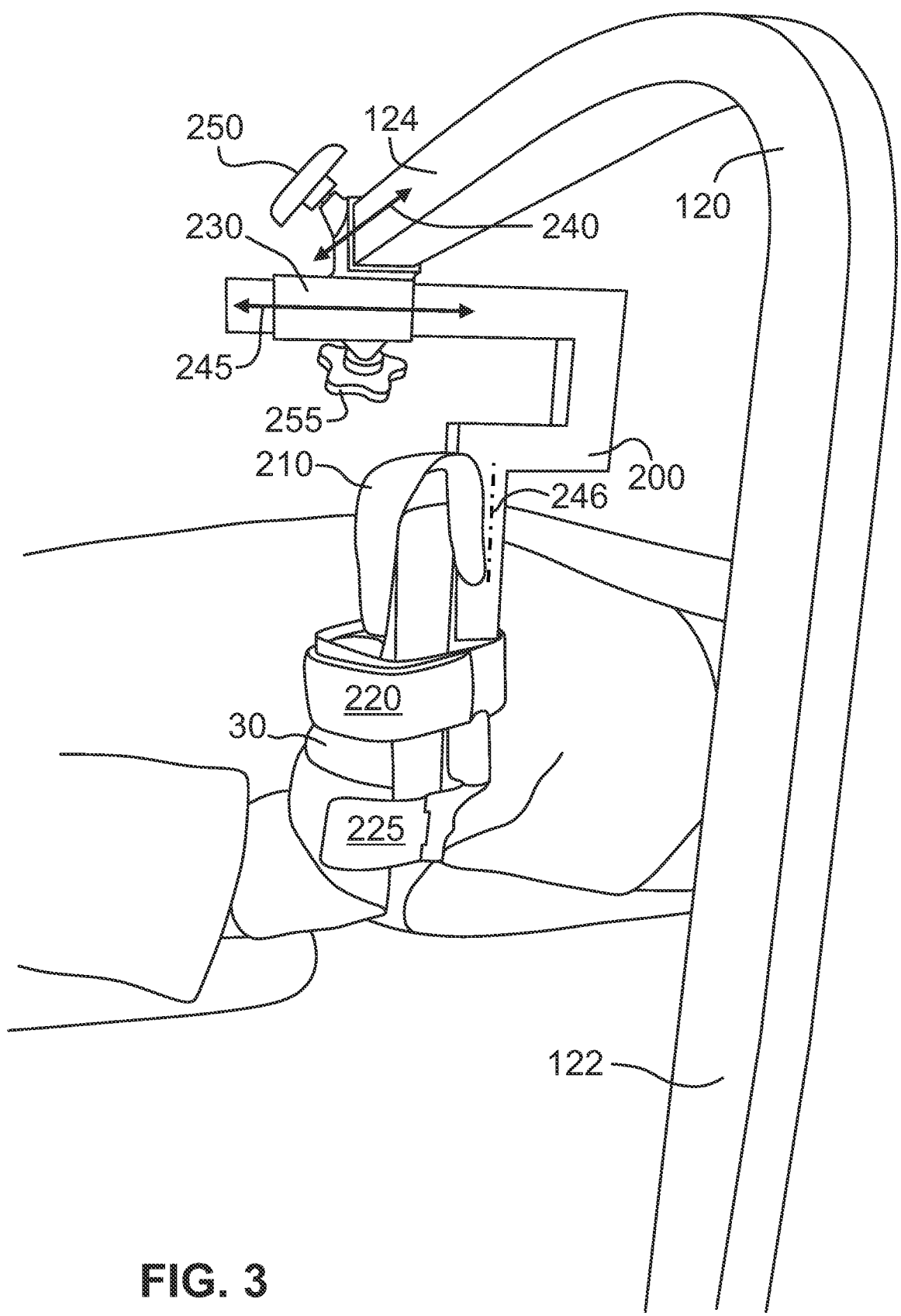
FIG. 3 is another photograph of a subject with an amputation below the elbow performing an elbow flexion/extension movement using an example dynamometer attachment configured to support an impaired limb.

An example embodiment of a dynamometer attachment for use with subjects having a limb impairment is shown in FIGS. 2-4. The adapter includes a frame 200 that has fixed thereto a padded limb support 210. The padded limb support 210 is configured to receive, and to removably secure, an impaired limb 30 of the subject (shown in FIG. 3), thereby reducing compression forces on the limb or residual limb. The padded limb support includes a restraining or securing mechanism for securing the impaired limb relative to the frame, such as straps 220 and 225. The frame is connected to the dynamometer lever arm 120 via an intermediate connector assembly 230.

As shown in FIGS. 2 and 3, the connector assembly 230 permits translation of the frame 200 in two dimensions relative to the lever arm 120 prior to securing the frame fixedly in place relative to the lever arm 120, where the two different directions of translation are shown as first direction 240 and second direction 245. The relative translation of the frame 200 permits the alignment of the padded limb support 210 with the impaired limb 30 prior to performing the movement with the dynamometer, while aligning the elbow joint of the subject with the rotation axis of the dynamometer. The first and second directions 240 and 245 may optionally be orthogonal, as shown in FIGS. 2 and 3. As shown in FIG. 2, a third direction of translational adjustability is provided by the connection of the lever arm 120 to the dynamometer 100, where connector 140 allows the lever arm to be varied in length relative to the rotation axis 105. In other example embodiments, such a connector may alternatively be integrated with the connector assembly, such that the connector assembly facilitates three-dimensional translational adjustment of the frame 200 relative to the dynamometer.

The translation adjustability of the attachment, in three different planes in relation to the isokinetic dynamometer, facilitates the alignment of the dynamometer attachment to the limb or partial limb of the subject without requiring movement of the subject, thereby providing significant benefit to the clinician and subject when preparing for use of the dynamometer.

The example connector assembly 230 shown in FIGS. 2 and 3 includes a first connector 250 that receives a distal portion of the lever arm 120, while permitting relative translation of the lever arm in the first direction 240 prior to securing the lever arm thereto. The first direction 240, as shown in FIG. 2, extends parallel to the rotation axis 105 of the dynamometer. Accordingly, when the subject is oriented relative to the dynamometer 100 as shown in FIGS. 2 and 3, with the sagittal plane of the subject residing perpendicular to the rotation axis 105 of the dynamometer, the first connector 250 permits alignment of the padded limb support 210 in a direction that is perpendicular to the sagittal plane. In the example implementation shown in FIGS. 2 and 3, the adjustability facilitates the positioning of the attachment closer or further from the plane of the shoulder and elbow. For individuals without a limb (and therefore no wrist), this ability is important as it allows for better alignment of the forearm in the same plane as the elbow and the shoulder.

The example lever arm shown in FIG. 3 includes a proximal lever arm portion 122 that is connected to the dynamometer, and a distal lever arm portion 124 that extends in a direction parallel to the rotation axis 105 of the dynamometer 100. In such a configuration, the first connector 250 may be configured to receive a distal region of the distal lever arm portion 125. It will be understood, however, that other configurations of the lever arm may be employed without departing from the intended scope of the present disclosure.

The example connector assembly shown in FIGS. 2 and 3 also includes a second connector 255 that receives a distal portion of the frame 200, while permitting relative translation of the frame in the second direction 245 prior to securing the frame thereto. In the example embodiment shown in FIGS. 2 and 3, the second direction 245 extends perpendicular to the rotation axis 105 of the dynamometer and perpendicular to the lever axis 125 (shown in FIG. 2) of the lever arm 120. Accordingly, when the subject is placed as shown in FIG. 2, in a prone position with sagittal plane of the subject residing perpendicular to the rotation axis 105 of the dynamometer 100, the second connector 255 permits alignment of the padded limb support 210 in a direction that is perpendicular to the transverse (axial) plane.

Figure 4A:
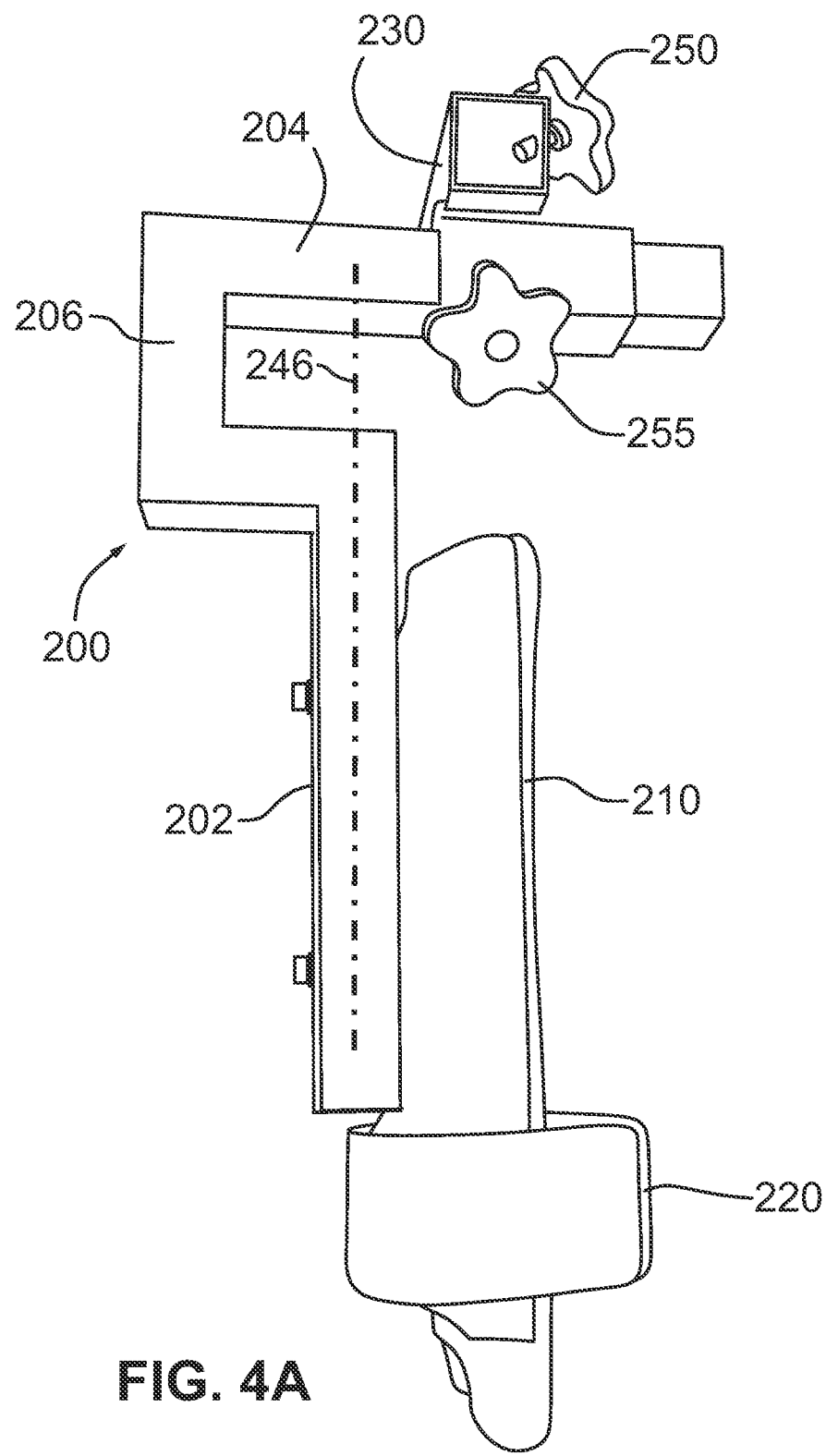
FIG. 4A is a photograph of an example dynamometer attachment configured for use with a subject having an impaired limb.
Figure 4B:
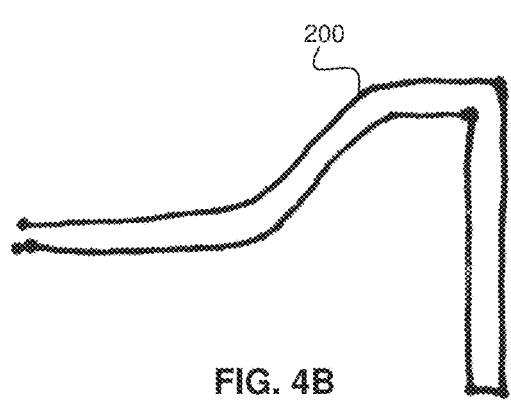
FIGS. 4B-E illustrate various example alternative shapes for the frame of the dynamometer attachment.
Figure 4C:
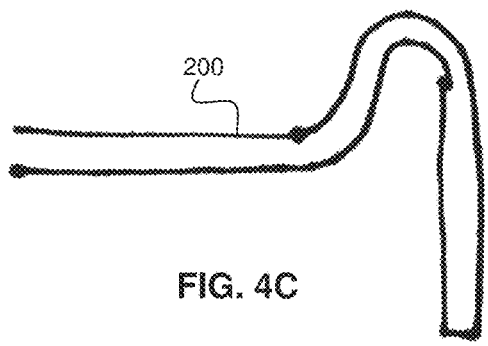
Figure 4D:
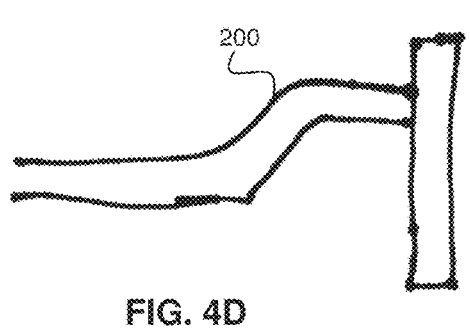
Figure 4E:
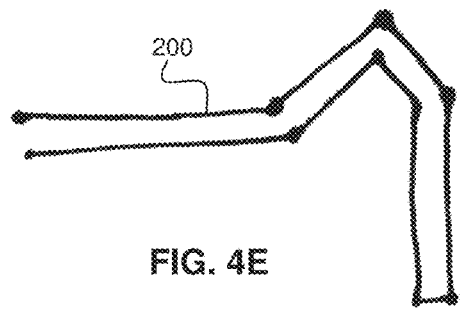

As shown in FIG. 4A, where the example attachment device is shown separated from the lever arm, the frame 200 may include an elongate proximal portion 202 extending along a third direction 246 that is perpendicular to the first direction 240 and the second direction 245 (shown in FIGS. 2 and 3), and an elongate distal portion 204 extending along second direction. As shown in FIG. 2, the third direction 246 is parallel to the lever axis 125 of the lever arm 120. As shown in FIG. 4A, the second connector 255 is configured to receive the elongate distal portion 204 of the frame 200 prior to securing the frame 200.

FIG. 4A also shows an example configuration of the frame in which the elongate proximal portion 202 and the elongate distal portion 204 are connected through an offsetting member 206, where the offsetting member enables the padded limb support 210 to be positioned beneath the second connector 255 in the absence of interference with the second connector 255. As can be seen in FIG. 4A, the offsetting member 206 is configured such that an axis associate with the elongate proximal portion (along the third direction 246) passes through an intermediate region of the elongate distal portion 204 of the frame. Various nonlimiting alternative example configurations for the frame 200 that also include a spatial offset are illustrated in FIGS. 4B-E.

As shown in FIG. 4A, the padded limb support 210 is fixed to the frame 200. In the example embodiment shown, the padded limb support 210 is fixed by fasteners to the elongate proximal portion 202 of the frame 200, although other methods may alternatively be employed, such as an adhesive. The padded limb support 210 is configured to receive and detachably secure the limb (or partial limb) of the subject. The padded limb support 210 may include a curved support (described in further detail below) configured to conform the shape of a subject's limb and cushioning material provided on or surrounding the curved support. Nonlimiting examples of suitable padding materials include foam (e.g. memory foam), neoprene, gels, feathers, and viscous liquids having an enclosure or covering material. The padded limb support 210 may optionally include a cover that is removable for cleaning or washing. The restraining mechanism may be any suitable mechanism that comfortably restrains the subject's limb or partial limb during dynamometer movements. Non-limiting examples of suitable restraining mechanisms include velcro straps and laces.

In some example implementations, the padded limb support 210 (e.g. the curved support) may be adjustable in width, length, and/or curvature in order to accommodate different limb shapes and sizes of different subjects, or different limbs of a given subject. For example, the width and/or curvature of the padded limb support 210 could be adjustable via the use of flexible/stretchable material, as well as some strapping to allow for individual comfort. Adjustability of the length of the padded limb support 210 could be achieved, for example, by the use of a thin, collapsible material (such as two plates that could slide over one another) extending or collapsing to the appropriate length. In an alternative example embodiment, a number of differently sized and/or shaped attachments could be provided, where a given attachment having the best fit is selected for a given subject.

In one example embodiment, the padded limb support 210 may be customized for a given limb. For example, the padded limb support 210 may be customized for upper limb amputees having an amputation below the elbow. In another example implementation, the padded limb support 210 may be customized for upper limb amputees having an amputation above the elbow. In another example implementation, the padded limb support 210 may be customized for lower limb amputees having an amputation below the knee. In another example implementation, the padded limb support 210 may be customized for lower limb amputees having an amputation above the knee.

In one example embodiment, the padded limb support 210 may be customized to a selected limb (or partial limb) of a given subject. For example, a base of the padded limb support may be cast (or otherwise formed, such as via three-dimensional printing) according to the shape of a selected limb or partial limb (and optionally a prosthesis) of a subject.

The frame 200 may be formed according to a wide variety of configurations and materials, of which the frame 200 shown in FIGS. 2-4 is a non-limiting example. In some example implementations, the frame 200 may be formed from metal tubing. The metal tubing may have a square cross-section as shown in FIGS. 2-4, or alternatively a non-square cross-section, such as, but not limited to, a circular cross-section.

The connector assembly 230 shown in FIGS. 2-4, which permits relative translation of both the lever arm 120 and the frame 200, may be configured according to a wide variety of implementations beyond the example embodiment shown in FIGS. 2-4. In the example embodiment shown in FIGS. 2-4, the connector assembly includes a first aperture configured to slidably receive a distal portion of the lever arm 210, and a second aperture configured to slidably receive a distal portion of the frame 200. The first and second connectors may be provided according to a wide variety of different embodiments other than the screw-based mechanism shown in FIGS. 2-4, such as using a clamping mechanism, a quick release clamp, a cotter pin, and a fastener (such as, for example, a threaded rod, bolt, or pin).

Figures 5A, 5B:
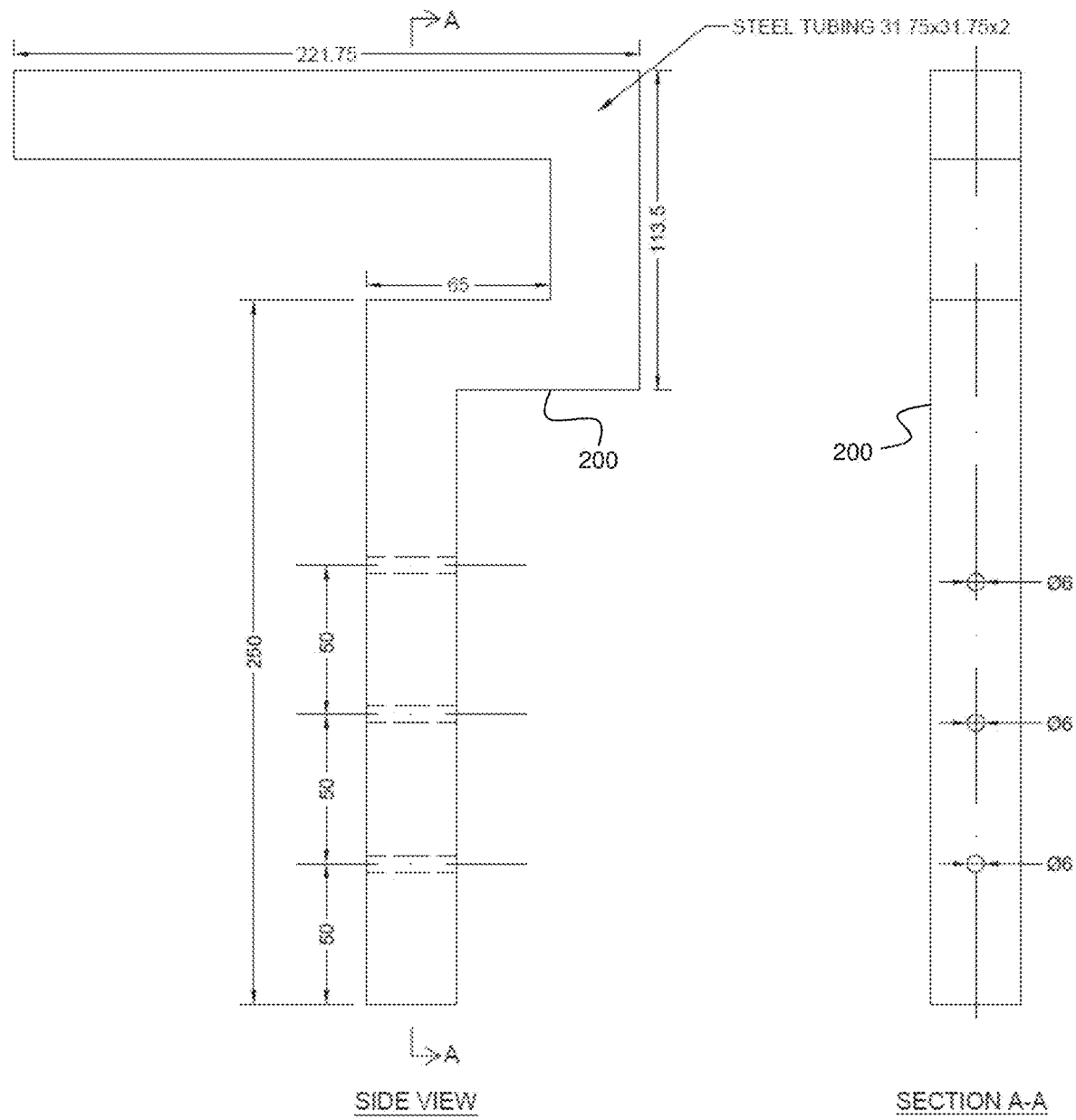
FIGS. 5A and 5B show different views of a frame that forms a component of an example dynamometer attachment, where the dynamometer attachment is configured for use with a subject having an impaired limb, and where the frame is configured to secure a padded limb support.
Figure 6A:
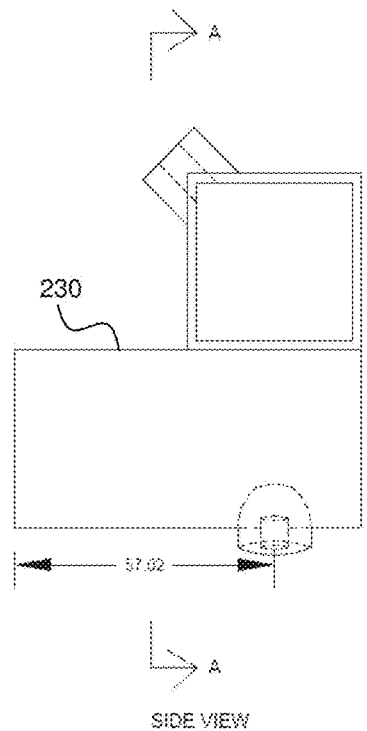
FIGS. 6A-C show different views of a connector assembly that forms a component of an example dynamometer attachment, where the dynamometer attachment is configured for use with a subject having an impaired limb, and where the frame is configured to secure a padded limb support.
Figure 6B:
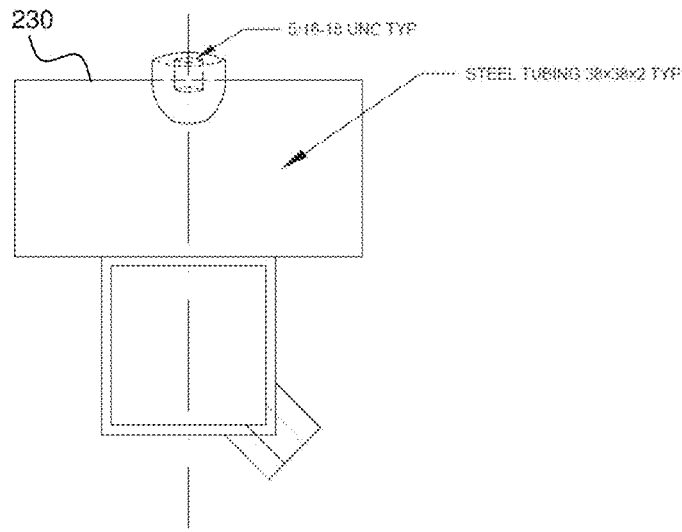
Figure 6C:
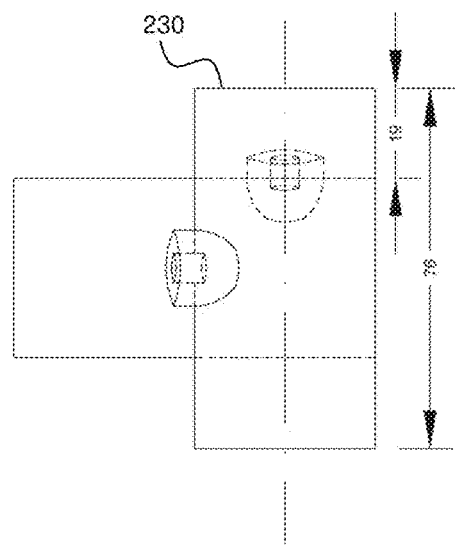

Referring now to FIGS. 5A and 5B, drawings are provided on an example and non-limiting configuration of the frame 200. FIGS. 6A-C show an example configuration of the connector assembly 230.

FIGS. 7A-7C illustrate an example implementation of a curved support 260 to which padding is secured, thereby forming the padded limb support. The example curved support has a curvature selected to accommodate a limb or range of limb sizes, and is attachable to the frame via a base portion 265, shown in FIG. 7C. As shown in FIG. 7A, the curved limb support 260 may include a proximal aperture 270 that is configured to permit rotation of a joint of the subject when the device is secured to a limb of the subject. For example, the aperture 270 may permit the rotation of the elbow joint when the padded limb support is secured to the forearm of a subject.

Figure 8:
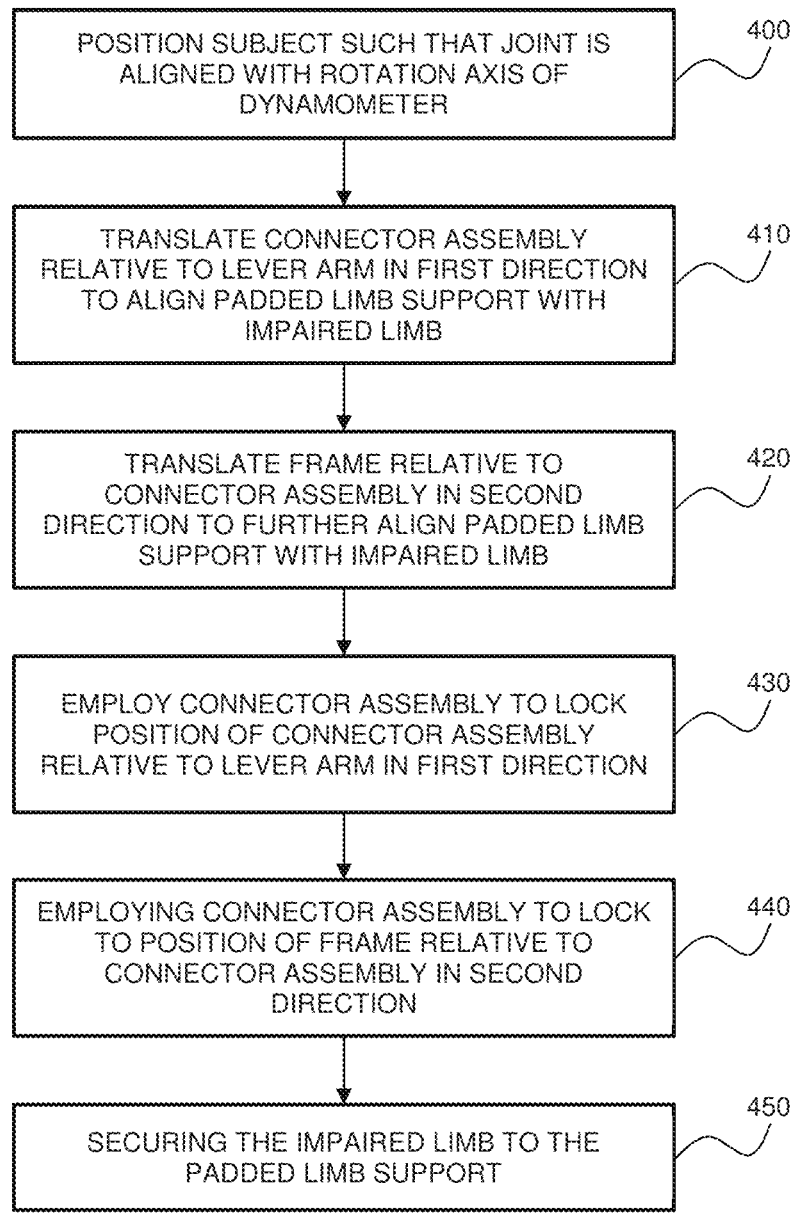
FIG. 8 is a flow chart that illustrates an example method of aligning a subject with a dynamometer attachment prior to performing a movement involving a joint associated with an impaired limb of the subject.

Referring now to FIG. 8, a flow chart is provided that illustrates an example method of aligning a subject with a dynamometer attachment prior to performing a movement involving a joint associated with an impaired limb of the subject. In step 400, the subject is positioned such that the joint is aligned with the rotation axis of the dynamometer. The dynamometer attachment, configured according to any of the preceding embodiments or variations thereof, is then aligned by: translating the connector assembly relative to the lever arm in the first direction (parallel to the rotation axis of the dynamometer) to initially align the padded limb support with the impaired limb as shown at step 410, and translating the frame relative to the connector assembly in the second direction (perpendicular to the rotation axis of the dynamometer and the lever axis of the lever arm) to further align the padded limb support with the impaired limb, as shown at step 420. As shown respectively at steps 430 and 440, the connector assembly may then be employed to: lock the position of the connector assembly relative to the lever arm in the first direction, and lock to position of the frame relative to the connector assembly in the second direction. The impaired limb of the subject is then secured to the padded limb support, as shown at step 450. It will be understood that the ordering of steps 410 and 420 may be reversed, and that step 430 may be performed after performing step 410 (prior to translating the frame relative to the connector assembly). Furthermore, the dynamometer attachment may be further aligned in the direction associated with the lever axis by translating the lever arm relative to the connector employed to connect the lever arm to the dynamometer.

The example attachments disclosed herein may be employed with a wide variety of commercial and research-grade dynamometers, such as those provided by Cybex, Biodex and Kin-con. In some example implementations, the present adapters may be employed for using with amputate subjects in conjunction with surface electromyography (EMG) for testing controlled, dynamic movements.

Although many of the preceding example embodiments have been described with reference to isokinetic movements, it will be understood that the attachments disclosed herein may be additionally or alternatively employed for performing isometric measurements or exercises.

Furthermore, while the example embodiments illustrated in FIGS. 2 and 3 illustrate the use of an attachment for isokinetic elbow flexion/extension movements, it will be understood that a wide variety of movements may be employed using the attachments described herein, or variations thereof. In one example implementation, the attachment can be adapted for use in performing a shoulder abduction/adduction movement (shoulder toward and away from midline), or a shoulder extension/flexion movement. Such example implementations may benefit from lengthening the frame and the lever arm to allow the shoulder to complete the rotation. It is noted that shoulder flexion is the movement of the arms from rest (by the side of the body) to straight above the head, while shoulder extension is the movement of the arms to straight behind. In another example implementation, the attachments described herein could be adapted for use with pronation and supination movements of the forearm.

In another example implementation, the attachments described herein may be adapted for performing lower limb movements. While the example attachment shown in FIGS. 2-4 was developed for upper limb movements, it can also be adapted for lower limb movements. For example, the attachment could be adapted with a padded limb support (sleeve) to (at least partially) encapsulate or surround the residual limb of the leg (below the knee). Such an adaptation could be employed to facilitate lower limb movements including knee extension/flexion (seated or prone) and tibial internal/external rotation. Alternatively, the attachment could be configured for supporting the lower limb above the knee, for example, for performing hip flexion movements. It will be understood that aforementioned movements are not intended to be limiting, and that the attachments described herein may be adapted for other types of movements (for example, for different types of exercise, therapy, or assessment).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An isokinetic dynamometer attachment for use with a subject having a limb impairment, the isokinetic dynamometer attachment comprising:
    a frame;
    a padded limb support fixed to said frame; and
    a connector assembly for connecting said frame to a lever arm of an isokinetic dynamometer, wherein the connector assembly is configured to permit independent translation of said frame in two directions relative to the lever arm after engaging said connector assembly with the lever arm but prior to securing said frame fixedly to the lever arm, the two orthogonal directions being fixed relative to the lever arm, thereby facilitating alignment of said padded limb support with an impaired limb of the subject while aligning a joint of the subject with a rotational axis of the isokinetic dynamometer;
    wherein said padded limb support is capable of receiving and removably securing an impaired limb of the subject such that movement of the isokinetic dynamometer by the subject is facilitated in the absence of a functioning distal portion of the impaired limb.

2. The isokinetic dynamometer attachment according to claim 1 wherein the connector assembly comprises:
    a first connector configured to receive a distal portion of the lever arm and to permit relative translation of the lever arm in the first direction prior to securing the lever arm thereto; and
    a second connector configured to receive a portion of said frame and to permit relative translation of said frame in the second direction prior to securing said frame thereto.

3. The isokinetic dynamometer attachment according to claim 2 wherein the first direction and the second direction are orthogonal.

4. The isokinetic dynamometer attachment according to claim 2 wherein the connector assembly is configured such that when the lever arm is connected to the isokinetic dynamometer, the first direction is parallel to the rotational axis of the isokinetic dynamometer, and the second direction is orthogonal to the rotational axis of the isokinetic dynamometer.

5. The isokinetic dynamometer attachment according to claim 2 wherein said frame comprises:
    an elongate proximal portion extending along a third direction that is perpendicular to the first direction and the second direction; and
    an elongate distal portion extending along the second direction;
    wherein said padded limb support is secured to said elongate proximal portion; and
    wherein said second connector is configured to receive said elongate distal portion and to permit relative translation of said elongate distal portion in the second direction prior to securing said elongate distal portion.

6. The isokinetic dynamometer attachment according to claim 5 wherein said elongate distal portion and said elongate proximal portion are connected through an offsetting member configured such that an axis associated with said elongate proximal portion passes through an intermediate region of said elongate distal portion, thereby permitting said padded limb support to be positioned beneath said second connector in absence of interference with said second connector.

7. The isokinetic dynamometer attachment according to claim 2 wherein said frame is formed from metal tubing, and wherein said second connector comprises an aperture configured to slidably receive and detachably secure said metal tubing.

8. The isokinetic dynamometer attachment according to claim 1 wherein said padded limb support is configured to receive and secure a portion of an upper limb.

9. The isokinetic dynamometer attachment according to claim 1 wherein said padded limb support is configured to receive and secure at least a portion of a forearm.

10. The isokinetic dynamometer attachment according to claim 1 wherein said padded limb support is configured to receive and secure at least a portion of an upper arm region located above the elbow joint.

11. The isokinetic dynamometer attachment according to claim 1 wherein said padded limb support is configured to receive and secure a portion of a lower limb.

12. The isokinetic dynamometer attachment according to claim 1 wherein said padded limb support is configured to receive and secure at least a portion of a lower leg region located below the knee joint.

13. The isokinetic dynamometer attachment according to claim 1 wherein said padded limb support is configured to receive and secure at least a portion of an upper leg region located above the knee joint.

14. An isokinetic dynamometer system for use with a subject having a limb impairment, the isokinetic dynamometer system comprising:
- an isokinetic dynamometer;
- a lever arm connected to said isokinetic dynamometer, said lever arm comprising at least a proximal lever arm portion extending along a lever axis perpendicular to a rotation axis of said isokinetic dynamometer;
- a frame;
- a padded limb support fixed to said frame; and
- a connector assembly for connecting said frame to a distal portion of said lever arm, wherein the connector assembly is configured to permit independent translation of said frame in a first direction parallel to the rotation axis and a second direction perpendicular to the lever axis and perpendicular to the rotation axis after engaging said connector assembly with said lever arm but prior to securing said frame fixedly to the lever arm, the two orthogonal directions being fixed relative to the lever arm, thereby facilitating alignment of said padded limb support with an impaired limb of the subject while aligning a joint of the subject with a rotational axis of said isokinetic dynamometer;
- wherein said padded limb support is capable of receiving and removably securing an impaired limb of the subject such that movement of the isokinetic dynamometer by the subject is facilitated in the absence of a functioning distal portion of the impaired limb.

15. The isokinetic dynamometer system according to claim 14 wherein the connector assembly comprises:
- a first connector configured to receive said distal portion of said lever arm and to permit relative translation of said lever arm in the first direction prior to securing said lever arm thereto; and
- a second connector configured to receive a portion of said frame and to permit relative translation of said frame in the second direction prior to securing said frame thereto.

16. The isokinetic dynamometer system according to claim 15 wherein said lever arm further comprises a distal lever arm portion extending parallel to the rotation axis, and wherein said first connector is configured to receive a distal region of said distal lever arm portion.

17. The isokinetic dynamometer system according to claim 15 wherein said frame comprises:
- an elongate proximal portion extending along a third direction that is perpendicular to the first direction and the second direction; and
- an elongate distal portion extending along the second direction;
- wherein said padded limb support is secured to said elongate proximal portion; and
- wherein said second connector is configured to receive said elongate distal portion and to permit relative translation of said elongate distal portion in the second direction prior to securing said elongate distal portion.

18. The isokinetic dynamometer system according to claim 17 wherein said elongate distal portion and said elongate proximal portion are connected through an offsetting member configured such that an axis associated with said elongate proximal portion passes through an intermediate region of said elongate distal portion, thereby permitting said padded limb support to be positioned beneath said second connector in absence of interference with said second connector.

19. The isokinetic dynamometer system according to claim 15 wherein said lever arm is extendable along the lever axis.

20. A method of aligning a subject with an isokinetic dynamometer prior to performing a movement involving a joint associated with an impaired limb of the subject, the method comprising:
- providing an isokinetic dynamometer system according to claim 14;
- positioning the subject such that the joint is aligned with the rotation axis of the isokinetic dynamometer;
- translating the connector assembly relative to the lever arm in the first direction to align the padded limb support with the impaired limb;
- translating the frame relative to the connector assembly in the second direction to further align the padded limb support with the impaired limb;
- employing the connector assembly to lock the position of the connector assembly relative to the lever arm in the first direction;
- employing the connector assembly to lock to position of the frame relative to the connector assembly in the second direction; and
- securing the impaired limb to the padded limb support.

* * * * *